US006462021B1

(12) United States Patent
Gustafsson

(10) Patent No.: US 6,462,021 B1
(45) Date of Patent: Oct. 8, 2002

(54) USE OF LOW MOLECULAR WEIGHT THROMBIN INHIBITOR

(75) Inventor: David Gustafsson, Kullavik (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/705,912

(22) Filed: Nov. 6, 2000

(51) Int. Cl.$^7$ .......................... C07K 5/00; A61K 38/55
(52) U.S. Cl. .............................. 514/18; 514/18; 514/2; 514/210; 530/300; 530/310; 530/380; 530/382; 548/953; 435/214
(58) Field of Search ................................ 514/2, 18, 19, 514/210; 435/214; 548/953; 530/380, 382, 300, 331

(56) References Cited

FOREIGN PATENT DOCUMENTS

| WO | 94/29336 | 12/1994 |
| --- | --- | --- |
| WO | 96/14084 | 5/1996 |
| WO | 96/16671 | 6/1996 |
| WO | 97/15190 | 5/1997 |
| WO | 97/23499 | 7/1997 |
| WO | 97/39770 | 10/1997 |
| WO | 9745138 | 12/1997 |
| WO | 98/16252 | 4/1998 |
| WO | 99/27912 | 6/1999 |
| WO | 99/27913 | 6/1999 |
| WO | 00/12043 | 3/2000 |
| WO | 00/13671 | 3/2000 |
| WO | 00/41716 | 7/2000 |

OTHER PUBLICATIONS

Presentation to Analysts, Dec. 1999, Development Strategy H 376/95—Chronic Indications.
Presentation, Sep. 29, 2000, "Clinical Trials Program".
Schulman, S., "Oral Thrombin Inhibitors," Haemostasis, vol. 30, No. 9, (2000), Abstract.
Thomson, et al, "Decision analysis and guidelines for anticoagulant . . . ," The Lancet, vol. 355, No. 9208, pp. 956–962 (2000), Abstract.
McBridge, "Adjusted–dose warfarin versus low-intensity . . . ," The Lancet, vol. 348, No. 9028, pp. 633–638 (1996), Abstract.
Levine et al, "Double–blind randomised trial of very-low–dose warfarin . . . ," The Lancet, vol. 343, No. 8902, pp. 886–889 (1994), Abstract.
Lip, G., "Thromboprophylaxis for atrial fibrillation," The Lancet, vol. 353, No. 9164, pp. 1620–1621 (1999), Title.
Dalton, R.G., "Thromboprophylaxis for artrial . . . ," The Lancet, vol. 353, No. 9154, p. 756 (1999), Title.
Lip, G.,"Thromboprohylaxis for artrial . . . ," The Lancet, vol. 353, No. 9146, pp. 4–6 (1999), Title.
Toh et al, "Artrial fibrillation," The Lancet, vol. 352, No. 9143, p. 1858 (1998), Title.
Morocutti et al, "Aspirin and prevention of stroke," The Lancet, vol. 343, No. 8891, pp. 234–234 (1994), Title.

Laupacis–Andreas, "Commentary: Anticoagulants for artrial fibrillation," The Lancet, vol. 342, No. 8882, pp. 1251–1252 (1993), Title.
OConnell et al, "Letters to the Editor: Atrial fibrillation and cognitive . . . ," The lancet, vol. 340, No. 8828, p. 1169 (1992). Title.
Fisher, C., "Letters to the Editor: Stroke," The Lancet, vol. 339, No. 8801, pp. 1112–1113 (1992), Title.
Hart, R., "Stroke Octet: Cardiogenic embolism . . . ," The Lancet, vol. 339, N. 8793, pp. 589–594 (1992). Title.
Sandercock, P., "Letters to the Editor: Aspirin, warfarin . . . ," The Lancet, vol. 388, n. 8759, p. 124 (1991), Title.
Flegel et al, "Original Articles: Risk of stroke in . . . ," The Lancet, vol. 329, No. 8532, pp. 526–529 (1987), Abstract.
Sandercock et al, "Trial design: Is a controlled trial of long term . . . ," The Lancet, vol. 327, No. 8484, pp. 788–792 (1986), Title.
"The Lancet: Is lone artrial fibrillation really benign," The Lancet, vol. 327, No. 8476, pp. 305–306 (1986), Title.
Thomson et al, "Decision analysis and guidelines for anticoagulant . . . ," The Lancet, vol. 355, No. 9208, pp. 956–962 (2000) (with text).
Leys, D., "Prevention of cerebral ischemia: anti–platelet agents," Revue neurologique (France), vol. 155, No. 9, pp. 688–93 (1999), Abstract.
Crassard et al, "Antiplatelet drugs for prevention of cerebral . . . ," Revue neurologique (France), vol. 155, No. 8, pp. 531–41 (1999), Abstract.
Gershlick, AH "Treating the non–electrical risks of atrial fibrillation," European Heart Journal (England), 18 Suppl. C p. C19–26 (1997), Abstract.
Chalon et al, "Antithrombotic therapy of atrial fibrillation," Archives des maladies du coeur et des vaisseaux (France), vol. 89 (11 Suppl) p. 1533–42 (1996), Abstract.
Cattaneo, M., "Prevention of thromoembolism . . . ," Annali italiani di medicina interna (Italy) 11 Suppl 2, p. 15S–17S (1996), Abstract.
Lardoux et al, "Spontaneous intracardiac contrast and embolic risk . . . ," Archives des maladies du coeur et des vaisseaux (France), vol. 89, No. 4, p. 451–7 (1996), Abstract.
Codinach, H., "Atrial fibrillation due to non–valvular . . . ," Medicina clinica (Spain), vol. 106, No. 15, pp. 586–589 (1996), Title Descriptors.
Martin, R., "Non–valvular fibrillation and cerebral . . . ," Revista de neurologia (Spain), vol. 23, No. 120 pp. 370–376 (1995), Abstract.

(List continued on next page.)

Primary Examiner—Karen Cochrane Carlson
Assistant Examiner—Chih-Min Kam
(74) Attorney, Agent, or Firm—Nixon & Vanderhye

(57) ABSTRACT

According to the invention there is provided the use of melagatran, or a pharmaceutically-acceptable derivative thereof, for the manufacture of a medicament for the treatment of ischemic disorders in patients having, or at risk of, non-valvular atrial fibrillation.

9 Claims, 1 Drawing Sheet

OTHER PUBLICATIONS

Figure 1:
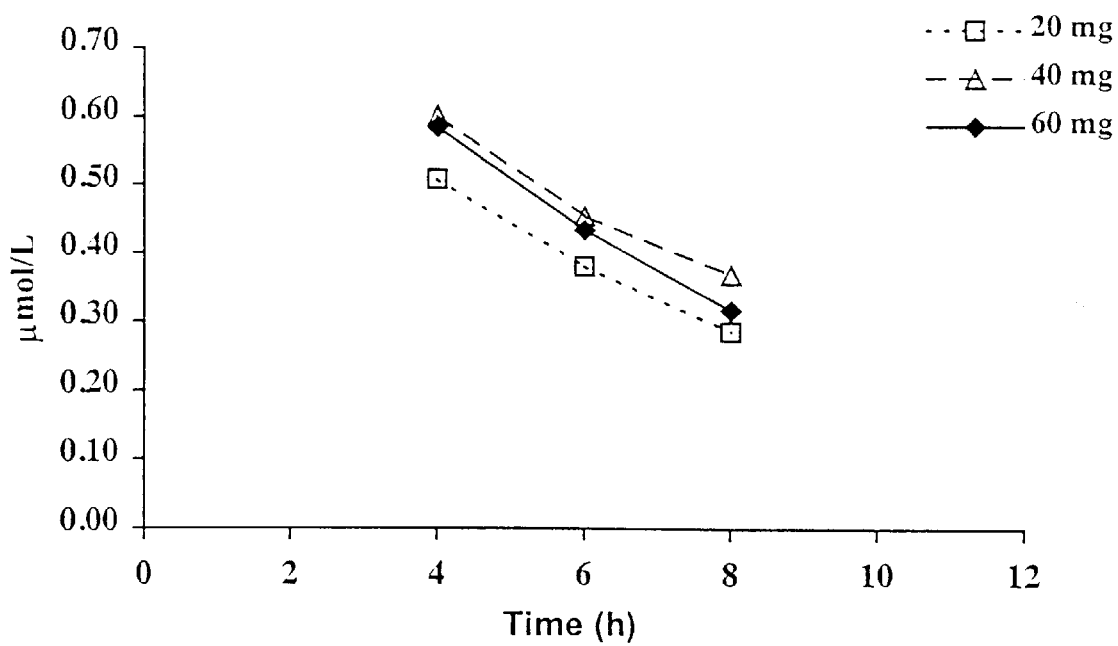

Chollet, F., "From heart to brain and from brain to heart: impact . . . ," La Presse medicale (France) vol. 23, No. 13, pp. 618–22 (1994), Abstract.

Lardoux et al, "Reducation of artrial fibrillation. New concepts, new . . . ," La Presse medicale (France) vol. 24, No. 38, pp. 1820–1823 (1995), Abstract.

Dahl et al, "Antithrombotic therapy in cerebrovascular . . . ," Tidsskrift for den Norske laegeforening (Norway) vol. 115, No. 23, pp. 2909–2912 (1955), Abstract.

Mas, J.L., "Thromboembolic complications in the course . . . ," La Revue du praticien (France), vol. 45, No. 8, pp. 935–941 (1995), Title Descriptors.

Zuber et al, "Epidemiology of cerebral infarction," Annales de radiologie (France) vol. 37, No. 1–2, pp. 7–10 (1994), Abstract.

Besdine, R.W., "Stroke prevention in the elderly," Connecticut medicine (U.S.), vol. 57, pp. 287–292 (1993), Abstract.

Sila, C.A., "Prophylaxis and treatment of stroke. The state of the . . . ," Drugs (New Zealand), vol. 45, No. 3, pp. 329–337 (1993), Abstract.

Une, F., "Nuclear magnetic resonance image and CT . . . ," Nippon rinsho (Japan), 51 Suppl., pp. 874–878 (1993), Title Descriptors.

Nighoghossian et al, "Ataxic monoparesis of the upper limb and suspension . . . ," Revue neurologique (France), vol. 149, No. 4, pp. 262–266 (1993), Abstract.

"ICD (implantable cardioverter defibrillator) . . . ," Clinica, Jun. 23, 2000, Abstract.

"FDA approves Medtronic's Jewel ICD (implantable . . . ," Clinica, Jun. 22, 2000.

"Cardima launches ablation microcatheter in Europe . . . ," Clinica, Jun. 20, 2000.

"St. Jude warns doctors of technical faults in pacemakers," Clinica, Jun. 9, 2000.

"Diltiazem for stroke prevention?" Strip, Jun. 7, 2000.

"European approvals for cardiac stimulation devices," Clinica, Jun. 1, 2000.

USE OF LOW MOLECULAR WEIGHT THROMBIN INHIBITOR

This invention relates to a new use of the low molecular weight thrombin inhibitor, melagatran and derivatives thereof.

Atrial fibrillation (AF) is characterised by grossly disorganised atrial electrical activity that is irregular in respect of both rate and rhythm. Patients with AF have no visually discernible timing pattern in atrial electrical activity when measured by surface ECG, or in electrogram sequences recorded by catheter electrodes.

During AF, the regular pumping action of the atria is replaced by irregular, disorganised and quivering spasms of atrial tissue. These spasms may be experienced as irregular heartbeat, palpitations, discomfort, dizziness and/or angina pectoris. Further, the inefficient pumping action of the heart tends to lead to significant morbidity related to reduced blood flow. More seriously, the reduced cardiac output can lead to blood pooling in the left atria and the formation of blood clots. Blood clots, mostly originating in the left atrium, can dislodge as an embolism and travel through the bloodstream to organs, e.g. the brain, spleen, kidneys etc. If the embolism travels to the brain, this may result in cerebral stroke and even death.

In the U.S. alone, AF affects an estimated two million people, with approximately 160,000 new cases being diagnosed each year. It has been estimated that AF is responsible for over 70,000 strokes each year in the U.S., and that the cost of treating these patients is more than U.S.$3.6 billion annually. The cost of drug treatment for AF alone has been estimated to be in excess of U.S.$400 million world-wide each year.

AF can be classified in two broadly defined groups: "valvular" AF and "non-valvular" AF (NVAF). In valvular AF, the arrhythmia is experienced due to a disorder of one or more of the heart valves (e.g. valvular disease), or the presence of mechanical (prosthetic) heart valves. Conversely, NVAF is AF experienced in the case where there is an absence of significant valvular disease or prosthesis.

Current drug therapies for AF include antiarryhthmic drugs, administered with a view to re-establishing a normal heartbeat, and anticoagulant and/or thrombolytic drugs, administered with a view to preventing thromboembolism and/or cerebral stroke.

However, it is estimated that only 40% of patients with AF who should benefit from anticoagulant therapy do so, owing to the risks associated with existing treatments. This also includes patients whose anticoagulant therapy is in combination with cardioversion (electrical or chemical). In particular, of the currently-available oral anticoagulants, warfarin (a vitamin K antagonist) carries the risk of bleeding, and the need for frequent laboratory control. Vitamin K antagonists also demonstrate a notable risk of interaction with other drugs and certain foods, e.g. those that are rich in Vitamin K, and their use requires monitoring of the patient's blood coagulation status. Medication containing acetylsalicylic acid (an antiplatelet agent) also carries the risk of bleeding.

Thus, there is a need for alternative and/or better anticoagulant treatments for use in patients with, or at risk of, AF, and especially NVAF.

International patent application WO 94/29336 discloses a group of compounds that are useful as inhibitors of serine proteases, such as thrombin and/or kininogenases. The thrombin-inhibiting compounds are thus indicated as anticoagulants, and the kininogenase-inhibiting compounds as antiinflammatory agents.

One of the thrombin-inhibiting compounds that is specifically disclosed in WO 94129336 is HOOC—$CH_2$-(R) Cgl-Aze-Pab-H, which is also known as melagatran (see Example 1 of WO 94/29336, and the list of abbreviations in that document). International Patent Application WO 97/23499 discloses prodrugs of inter alia melagatran.

The use of melagatran and derivatives (including prodrugs) thereof in the treatment of thromboembolic events in patients with NVAF is not disclosed anywhere in the prior art.

We have now found that melagatran and derivatives thereof may be used in the treatment of thrombosis and/or thromboembolic events in patients with NVAF.

According to a first aspect of the invention there is provided the use of melagatran, or a pharmaceutically-acceptable derivative thereof, for the manufacture of a medicament for the treatment of an ischemic disorder, in a patient having, or at risk of, NVAF.

By patient "at risk of" NVAF, we include patients who are in danger of relapsing into NVAF.

For the avoidance of doubt, as used herein, the term "treatment" includes the therapeutic and/or prophylactic treatment of ischemic disorders.

"Pharmaceutically-acceptable derivatives" of melagatran include salts (e.g. pharmaceutically-acceptable non-toxic organic or inorganic acid addition salts) and solvates. It will be appreciated that the term further includes derivatives that have the same biological function and/or activity as melagatran. Moreover, for the purposes of this invention, the term also includes prodrugs of melagatran. The term "prodrug" includes any composition of matter that, following oral or parenteral administration, is metabolised in vivo to form melagatran in an experimentally-detectable amount, and within a predetermined time (e.g. within a dosing interval of between 6 and 24 hours (i.e. once to four times daily)). For the avoidance of doubt, the term "parenteral" adminstration includes all forms of adminstration other than oral administration. Prodrugs of melagatran that may be mentioned include those disclosed generically and specifically in international patent application WO 97/23499. Preferred prodrugs are those of the formula $R^1O_2C$—$CH_2$-(R)Cgl-Aze-Pab-OH (see the list of abbreviations in WO 97/23499), wherein $R^1$ represents $C_{1-10}$ alkyl or benzyl, such as linear or branched $C_{1-6}$ alkyl (e.g. $C_{1-4}$ alkyl, especially methyl, n-propyl, i-propyl, t-butyl and, particularly, ethyl) and the OH group replaces one of the amidino hydrogens in Pab.

The term "ischemic disorders" will be understood by those skilled in the art to include any condition, the results of which include a restriction in blood flow in a part of the body. In this context, the term will also be understood to include thrombosis and hypercoagulability in blood and/or organs, tissues, etc.

The term "thrombosis" will be understood by those skilled in the art to include the formation, development or presence of a thrombus in animals including man, and which may result in embolism and/or ischemia. The term may thus include conditions such as atrophic thrombosis, arterial thrombosis, cardiac thrombosis, coronary thrombosis, creeping thrombosis, infective thrombosis, mesenteric thrombosis, placental thrombosis, propagating thrombosis, traumatic thrombosis and venous thrombosis.

The term "hypercoagulability" includes any state in which the blood is more readily coagulated than usual.

The term "NVAF" may be understood by those skilled in the art to mean grossly disorganised atrial electrical activity, which is irregular in respect of both rate and rhythm, leading to a hypercoagulable state and an increased risk of thrombosis originating from the left heart chambers, and particularly the left atrium. The term may thus also be understood to include AF (chronic, persistent, permanent and/or intermittent (paroxysmal)) in the absence of heart valvular disease (mostly rheumatic heart valvular disease e.g. mitral stenosis), or prosthesis, and to exclude patients with rheumatic mitral stenosis.

Particular disease states that may be mentioned include the prevention/treatment of ischemic heart disease, myocardial infarction, systemic embolic events in e.g. the kidneys, spleen etc, and, more particularly, of cerebral ischemia, including cerebral thrombosis, cerebral embolism and/or cerebral ischemia associated with non-cerebral thrombosis or embolism (in other words, the treatment/prophylaxis of thrombotic, or ischemic, stroke and of transient ischemic attack (TIA)) in patients with, or at risk of, NVAF. The skilled person will appreciate that patients with NVAF who are at risk of stroke include elderly patients generally (e.g. those with an age of greater than 75 years); patients with complicating health factors, such as hypertension, left ventricular dysfunction (e.g. left ventricular ejection fraction (LVEF) of less than 40%), symptomatic congestive heart failure, diabetes mellitus (especially in those patients of 65 years of age or greater) and/or coronary heart or artery disease (especially in those patients of 65 years of age or greater); and/or patients with a history of stroke, TIA and/or systemic embolism, all of which factors may predispose such patients to stroke and/or thromboembolic events.

Melagatran, and derivatives thereof, may be administered for systemic delivery using appropriate means of administration that are known to the skilled person.

Thus, in accordance with the invention, melagatran, and derivatives thereof, may be administered orally, intravenously, subcutaneously, buccally, rectally, dermally, nasally, tracheally, bronchially, topically, by any other parenteral route, or via inhalation, in the form of a pharmaceutical preparation comprising the active ingredient in a pharmaceutically-acceptable dosage form. Depending on the disorder, and the patient, to be treated, as well as the route of administration, the compositions may be administered at varying doses.

Preferred modes of delivery are systemic. For melagatran, preferred modes of administration are parenteral, more preferably intravenously, and especially subcutaneous. For prodrugs of melagatran, preferred modes of administration are oral.

In the therapeutic treatment of mammals, and especially humans, melagatran and derivatives thereof may be administered alone, but will generally be administered as a pharmaceutical formulation in admixture with a pharmaceutically-acceptable adjuvant, diluent or carrier, which may be selected with due regard to the intended route of administration and standard pharmaceutical practice.

Suitable formulations for use in administering melagatran and derivatives (including prodrugs) thereof are described in the literature, for example as described in inter alia international patent applications WO 94/29336, WO 96/14084, WO 96/16671, WO 97/23499, WO 97/39770, WO 97/45138, WO 98/16252, WO 99/27912, WO 99/27913, WO 00/12043 and WO 00/13671, the disclosures in which documents are hereby incorporated by reference. Otherwise, the preparation of suitable formulations may be achieved non-inventively by the skilled person using routine techniques.

The amount of melagatran or derivative in the formulation will depend on the severity of the condition, and on the patient, to be treated, as well as the compound(s) which is/are employed, but may be determined non-inventively by the skilled person.

According to a further aspect of the invention there is provided a pharmaceutical formulation for use in the treatment of ischemic disorders in patients having, or at risk of, NVAF comprising an effective amount of melagatran or a pharmaceutically-acceptable derivative thereof in admixture with a pharmaceutically-acceptable adjuvant, diluent or carrier.

In the treatment of ischemic disorders, in patients with, or at risk of, NVAF, melagatran and derivatives (including prodrugs) thereof, may also be combined with other agents known for use in the treatment of conditions in which anticoagulant therapy is indicated, for example other thrombin inhibitors, or antithrombotic agents with a different mechanism of action, such as the antiplatelet agents acetylsalicylic acid, ticlopidine, clopidogrel, thromboxane receptor and/or synthetase inhibitors, fibrinogen receptor antagonists, prostacyclin mimetics and phosphodiesterase inhibitors and ADP-receptor ($P_2T$) antagonists. Melagatran and derivatives (including prodrugs) thereof may also be combined with agents that are known to be useful in the treatment of AF, and particularly NVAF, including known antiarrhythmic agents and heparins.

When melagatran, and derivatives thereof, are "combined" with other therapeutic agents in this way, the active ingredients may be administered together in the same formulation, or administered separately (simultaneously or sequentially) in different formulations.

Suitable doses of melagatran and derivatives thereof, in the therapeutic and/or prophylactic treatment of mammalian, especially human, patients may be determined routinely by the medical practitioner or other skilled person, and include the respective doses discussed in the prior art documents mentioned hereinbefore, the disclosures in which documents are hereby incorporated by reference.

For example, suitable doses of melagatran, prodrugs and derivatives thereof, in the therapeutic and/or prophylactic treatment of mammalian, especially human, patients include those which give a mean plasma concentration of up to 5 $\mu$mol/L, for example in the range 0.001 to 5 $\mu$mol/L (e.g. 0.01 to 1 $\mu$mol/L, such as 0.05 to 0.5 $\mu$mol/L) over the course of treatment of the relevant condition. Suitable doses may thus be in the range 0.1 mg once daily to 25 mg three times daily, and/or up to 100 mg infused parenterally over a 24 hour period, for melagatran, and in the range 0.1 mg once daily to 100 mg three times daily (e.g. 10 to 100 mg twice daily, such as 36 mg twice daily or thereabouts) for prodrugs of melagatran including those specifically mentioned herein.

In any event, the physician, or the skilled person, will be able to determine the actual dosage which will be most suitable for an individual patient, which is likely to vary with the condition that is to be treated, as well as the age, weight, sex and response of the particular patient to be treated. The above-mentioned dosages are exemplary of the average case; there can, of course, be individual instances where higher or lower dosage ranges are merited, and such are within the scope of this invention.

The skilled person will also appreciate that melagatran, or a derivative thereof, may be administered in an appropriate dose on an "as required" basis (i.e. as needed or desired).

According to a further aspect of the invention there is provided a method of preventing or treating an ischemic disorder in a patient having, or at risk of, NVAF, which comprises administering a therapeutically-effective amount of melagatran, or a pharmaceutically-acceptable derivative thereof, to a patient in need of such treatment.

The use and method described herein may have the advantage that, in the treatment of ischemic disorders in patients with, or at risk of, NVAF, melagatran and derivatives thereof may not possess disadvantages of known therapies. The use and method described herein may also have the advantage that melagatran and derivatives thereof may be more efficacious than, be less toxic than, have a broader range of activity than, be more potent than, produce fewer side effects than, be more easily absorbed than, or that they may have other useful pharmacological properties over, compounds known in the prior art for the treatment of ischemic disorders in patients with, or at risk of, NVAF.

The invention is illustrated, but in no way limited, by the following example, in which FIG. 1 shows mean plasma concentrations of melagatran with time following administration of particular doses of the prodrug compound $EtO_2C$—$CH_2$-(R)Cgl-Aze-Pab-OH.

EXAMPLE 1

Clinical Trial

This was a dose guiding study of Compound "X" ($EtO_2C$—$CH_2$-(R)Cgl-Aze-Pab-OH; a prodrug of the active thrombin inhibitor, melagatran; see Example 17 of WO 97/23499) given orally in NVAF. The tolerability of three different doses of X (20, 40, 60 mg p.o. b.i.d.) was compared with warfarin (aiming for an international normalisation ratio (INR) of 2 to 3) over 3 months' treatment in NVAF patients with moderately to high increased risk for stroke or systemic embolic events.

The target enrolment was 220 patients. Eligible patients were newly diagnosed or currently on warfarin or aspirin therapy.

The inclusion criteria for the study were:
1. History of chronic or intermittent NVAF verified by at least two ECG readings, separated by at least one week. The latest ECG was to be performed at randomisation.
2. In addition to 1 above, at least one of the following risk factors for stroke had to be present:
   hypertension
   age≧65 years
   any previous cerebral ischemic attack (stroke or transient ischemic attack [TIA])
   previous systemic embolism (defined as sudden vascular insufficiency of the limbs or internal organs associated with evidence of arterial occlusion in the absence of previous obstructive disease)
   left ventricular dysfunction (either left ventricular ejection fraction [LVEF]<40% or symptomatic congestive heart failure [CHF] within 3 months)
   diabetes mellitus
   coronary heart disease
3. Age≧18 years. No upper age limit
4. Weight 50 kg to 120 kg (approximately 110 to 265 lb.)

The main exclusion criteria were:
1. Stroke or TIA and/or systemic embolism within the previous 2 years.
2. AF secondary to other reversible disorders, e.g. hyperthyroidosis.
3. Mechanical heart valves.
4. Continuous non-steroidal anti-inflammatory drug (NSAID) treatment.
5. Contraindications for warfarin treatment.
6. Conditions associated with increased risk of bleeding, for example:
   history of intracranial bleeding
   history of bleeding gastrointestinal disorder and/or endoscopically-verified ulcer disease within the last year prior to inclusion
   major surgical procedure or trauma 2 weeks prior to inclusion
   known hemophilic disorder.
7. Diastolic blood pressure (DBP)>100 mm Hg or systolic blood pressure (SBP)>180 mm Hg.
8. Renal impairment (calculated creatinine clearance (Calc. CrCl.)<40 mL/min):

$$\text{Creatinine clearance} = \frac{b \times (140 - \text{age (years)}) \times \text{weight (kg)}}{\text{serum creatinine (µmol/L)}}$$

(in which b is 1.23 for males, 1.04 for females)
9. Known active liver disease or liver insufficiency.
10. Anemia (Hb<100 g/L).
11. Platelet count<$100 \times 10^9$/L.

This was a multicentre, multinational, randomized, parallel group, dose-guiding study to compare the safety and tolerabilty of X with warfarin in stroke prophylaxis in patients with NVAF.

Patients were split into four groups: one group receiving 20 mg of X b.i.d, one given 40 (2×20) mg of X b.i.d, and one 60 (3×20) mg of X b.i.d. The fourth group received warfarin (open label, INR aiming for 2.0 to 3.0). All X medication was given double blind (i.e. neither doctor nor patient knew what tablet strength of X was given).

The duration of treatment was 12 weeks. After the 12 week treatment period patients had the option of entering an open label following study on either 40 mg X b.i.d. (if assigned X) or warfarin (if assigned warfarin). The 40 mg b.i.d. dose was later reduced to 36 mg b.i.d. of X.

Results

Patient Disposition and Characteristics

A total of 257 patients were randomized at 32 sites in 11 countries and 254 received at least one dose of study drug. Forty-seven patients (19%) discontinued study drug prematurely and about 167 continued into an open follow-up study (Table 1).

TABLE 1

|  |  | Patient Disposition | | | | | | | | |
|---|---|---|---|---|---|---|---|---|---|---|
|  |  | 20 mg | | 40 mg | | 60 mg | | Warfarin | | Total | |
| Randomised | Yes | 66 | (100%) | 64 | (100%) | 60 | (100%) | 67 | (100%) | 257 | (100%) |
| Rec'd study drug | Yes | 66 | (100%) | 62 | (100%) | 59 | (100%) | 67 | (100%) | 254 | (100%) |
| Prematurely discont. | Yes | 10 | (15%) | 12 | (19%) | 12 | (20%) | 13 | (19%) | 47 | (19%) |

TABLE 1-continued

Patient Disposition

|  |  | 20 mg |  | 40 mg |  | 60 mg |  | Warfarin |  | Total |  |
|---|---|---|---|---|---|---|---|---|---|---|---|
| Cont. into later study | No | 18 | (27%) | 25 | (40%) | 19 | (32%) | 24 | (36%) | 86 | (34%) |
|  | Yes | 48 | (73%) | 37 | (60%) | 40 | (68%) | 42 | (63%) | 167 | (66%) |

The most frequent reasons for discontinuation are provided in Table 2. The number of discontinuations and the reasons for discontinuation were evenly distributed among the treatment groups.

TABLE 2

Reasons for Treatment Discontinuation

| | X Dose | | | |
|---|---|---|---|---|
| Number of Patients | 20 mg | 140 mg | 60 mg | Warfarin |
| Total Discontinued | 10 | 12 | 12 | 13 |
| Adverse Event | 6 | 3 | 5 | 4 |
| Calc. CrCl < 40 mL/min | 4 | 5 | 4 | 5 |
| Withdrawn Consent | 0 | 3 | 2 | 1 |
| Other | 0 | 1 | 1 | 3 |

Demographic characteristics are shown in Table 3. The patient population was primarily male (61%) and elderly (mean age 69.5, though the age range was 39 to 95) with a mean weight of 83 kg.

TABLE 3

Demographics

| | X Dose | | | | |
|---|---|---|---|---|---|
| Parameter | 20 mg n = 66 | 40 mg n = 62 | 60 mg n = 59 | Warfarin n = 67 | TOTAL N = 254 |
| Average age (years) | 69.9 | 69.7 | 68.4 | 70.0 | 69.5 |
| Age ≧ 65 (%) | 76 | 69 | 69 | 75 | 72 |
| Age ≧ 75 (%) | 26 | 31 | 20 | 31 | 27 |
| Males (%) | 65 | 68 | 54 | 55 | 61 |
| Weight (kg) | 85 | 85 | 82 | 80 | 83 |
| Calc. CrCl (mL/min) | 69 | 67 | 69 | 65 | 67 |

The duration of incidence of NVAF was over 1 year in most patients (73%) and was persistent in almost all (94%) (Table 4). About 80% of patients had between one to three additional risk factors for stroke (75%) with the most common being age ≧65 (72%), hypertension (57%), coronary heart disease (43%), and left ventricular dysfunction (31%)

TABLE 4

AF Characteristics

| | X Dose | | | | |
|---|---|---|---|---|---|
| Parameter | 20 mg | 40 mg | 60 mg | Warfarin | TOTAL |
| Duration AF (>1 year) (%) | 74 | 81 | 66 | 71 | 73 |

TABLE 4-continued

AF Characteristics

| | X Dose | | | | |
|---|---|---|---|---|---|
| Parameter | 20 mg | 40 mg | 60 mg | Warfarin | TOTAL |
| Persistent AF (%) | 95 | 98 | 93 | 91 | 94 |
| Multiple Risk Factors (%) | 77 | 69 | 80 | 74 | 75 |
| Previous Cardioversion Attempt (%) | 35 | 40 | 31 | 20 | 34 |

With regard to warfarin management, the percent of patients in the target INR range of 2.0 to 3.0 is displayed by study visit in Table 5. By Visit 7 (week 12) most patients (57%) were in the target range, with 31% having INR values below 2.0 and 12% having values greater than 3.0.

TABLE 5

Warfarin Management

| | | | INR Range | | |
|---|---|---|---|---|---|
| Visit | Week | N | 1.0–1.9 | 2.0–3.0 | >3.0 |
| 1 | 0 | 62 | 34 (55%) | 21 (34%) | 7 (11%) |
| 3 | 1 | 59 | 22 (37%) | 25 (42%) | 12 (20%) |
| 4 | 2 | 54 | 15 (28%) | 26 (48%) | 13 (24%) |
| 5 | 4 | 51 | 17 (33%) | 22 (43%) | 12 (24%) |
| 6 | 8 | 49 | 15 (31%) | 25 (51%) | 9 (18%) |
| 7 | 12 | 58 | 18 (31%) | 33 (57%) | 7 (12%) |

Efficacy Results

In the warfarin group, two TIAs were reported and in the X group, one is ischemic stroke and one TIA were reported (both at 60 mg b.i.d.; see Table 6. The estimated patient years of observation in the X group (all doses combined) was 40 years for a stroke rate of 2.5% (the annual stroke rate is about 3 to 4% in 65 year old persons not receiving treatment for NVAF, increasing to 10 to 12% in 85 year olds).

TABLE 6

Stroke/TIA Events

| Group | Pat. | Gender | Age | CrCl (mLmin) | Stroke/TIA | Prev. stroke | Prev. TIA |
|---|---|---|---|---|---|---|---|
| 60 mg | 121 | Male | 63 | 78 | Ischemic stroke | No | No |
| | 309 | Male | 65 | 89 | TIA | No | No |
| Warfarin | 120 | Male | 73 | 37 | TIA | No | No |
| | 153 | Female | 71 | 71 | TIA | No | No |

Safety Results

The number of unspecified (i.e. not marked as clinically overt on CRF), minor, and major bleeds are shown in Table 7. The only major bleed (genital tract) occurred in the warfarin group. The total number of bleeds and individual bleeding categories were comparable among the treatment groups. There did not appear to be any association between bleeding events and age, creatinine clearance, or gender.

TABLE 7

Bleeding Events

| | X Dose | | | | |
|---|---|---|---|---|---|
| Category | 20 mg | 40 mg | 60 mg | Warfarin | Total |
| None | 61 | 57 | 52 | 60 | 230 |
| Unspecified | 2 | 2 | 4 | 3 | 11 |
| Minor | 1 | 0 | 3 | 2 | 6 |
| Multiple Minor | 2 | 3 | 0 | 1 | 6 |
| Major | 0 | 0 | 0 | 1 | 1 |

The onset pattern of bleeding indicates that most bleeding on the 60 mg b.i.d. dose of X occurs early in the treatment period in a similar pattern to that seen with warfarin.

Reported adverse events included haematuria, increase in hepatic enzymes, dizziness, pain, diarrhoea, purpura, headache, nausea, fatigue, rash, abdominal pain, haemorrhoids, urinary tract infections, chest pain and vasospasm. The overall frequency of adverse events was low and there were no differences among the treatment groups.

A total of 29 serious adverse events (20 patients) were reported, including one fatal event (pneumonia unrelated to X). There did not appear to be any differences among the groups in the occurrence of non-cerebrovascular serious adverse events.

A few patients treated with X showed asymptomatic increases in liver enzyme levels.

Discussion

This study enrolled patients with NVAF and at least one additional risk factors for stroke. Demographic, medical history and AF characteristics were well balanced across the four treatment groups.

As expected, very few thromboembolic events (stroke, TIA or systemic emboli) were observed in this study due to the small sample size and short observation period. However, the lack of any excess events in the X groups suggests that X is promising for use in this indication. Only one major bleed was observed in the study (warfarin group) and the occurrence of minor bleeds was evenly distributed across all treatment groups.

The lack of increased bleeding at these dose levels suggests a shallow dose response for bleeding and a wide therapeutic index in agreement with animal models.

The pharmacokinetics of X in this population were dose proportional.

In conclusion, X was well tolerated at doses of up to 60 mg b.i.d. over 3 months. Melagatran and derivatives (including prodrugs) thereof provide promising alternatives to warfarin in the treatment of ischemic disorders in patients with NVAF.

(Results from ongoing trials, 1 year on from the date of the trial discussed above shows that a 36 mg b.i.d. dose of X (120 treatment years) has resulted in no major bleeds, 2 non-fatal strokes, and 2 TIAs in patients receiving X. In the warfarin group (40 treatment years), 3 major life-threatening bleeds, 2 fatal strokes and 2 TIAs have been reported.)

What is claimed is:

1. A method of treatment of an ischemic disorder in a patient having, or at risk of, non-valvular atrial fibrillation, which comprises administering a therapeutically effective amount of melagatran or a pharmaceutically-acceptable derivative of melagatran, said derivative having the inhibitory activity against thrombin or being a prodrug of melagatran, to a patient in need of such treatment for a time and under conditions suitable for reducing the incidence of said ischemic disorder.

2. A method as claimed in claim 1, wherein the ischemic disorder to be treated is cerebral ischemia.

3. A method as claimed in claim 2, wherein the ischemic disorder is thrombotic stroke, ischemic stroke, transient ischemic attack or systemic embolism.

4. A method as claimed in claim 1, wherein the derivative of melagatran is a salt of melagatran.

5. A method as claimed in claim 1, wherein the derivative of melagatran is a solvate of melagatran.

6. A method as claimed in claim 1, wherein the derivative of melagatran is a prodrug of melagatran.

7. A method as claimed in claim 6, wherein the prodrug is of the formula $R^1O_2C-CH_2-(R)Cgl-Aze-Pab-OH$ wherein $R^1$ is linear or branched $C_{1-6}$ alkyl, Cgl is cyclohexylglycine, Aze is S-azetidine-2-carboxylic acid and Pab-OH is 4-aminomethyl-benzamidoxime.

8. A method as claimed in 7, wherein $R^1$ is methyl, ethyl, n-propyl, i-propyl, or t-butyl.

9. A method as claimed in 7, wherein $R^1$ is ethyl.

* * * * *

UNITED STATES PATENT AND TRADEMARK OFFICE
CERTIFICATE OF CORRECTION

PATENT NO. : 6,462,021 B1
DATED : October 8, 2002
INVENTOR(S) : Andersson et al.

It is certified that error appears in the above-identified patent and that said Letters Patent is hereby corrected as shown below:

Column 2,
Line 4, please change "WO 94129336" to -- WO 94/29336 --.

Column 7,
Table 2, in the second column under X Dose, please change the header from "140 mg" to -- 40mg --.

Column 8,
Line 61, please change "Table 6." to -- Table 6). --

Signed and Sealed this

Fifteenth Day of July, 2003

JAMES E. ROGAN
*Director of the United States Patent and Trademark Office*